United States Patent
Allen et al.

(10) Patent No.: US 10,431,338 B2
(45) Date of Patent: *Oct. 1, 2019

(54) SYSTEM AND METHOD FOR WEIGHTING MANAGEABLE PATIENT ATTRIBUTES DURING CRITERIA EVALUATIONS FOR TREATMENT

(71) Applicant: International Business Machines Corporation, Armonk, NY (US)

(72) Inventors: Corville O. Allen, Morrisville, NC (US); Aspen L. Payton, Byron, MN (US)

(73) Assignee: International Business Machines Corporation, Armonk, NY (US)

( * ) Notice: Subject to any disclaimer, the term of this patent is extended or adjusted under 35 U.S.C. 154(b) by 836 days.

This patent is subject to a terminal disclaimer.

(21) Appl. No.: 14/692,504

(22) Filed: Apr. 21, 2015

(65) Prior Publication Data
US 2016/0246945 A1   Aug. 25, 2016

Related U.S. Application Data

(63) Continuation of application No. 14/630,751, filed on Feb. 25, 2015.

(51) Int. Cl.
*G16H 50/20* (2018.01)
*G06F 19/00* (2018.01)
*G16H 10/60* (2018.01)

(52) U.S. Cl.
CPC ......... *G16H 50/20* (2018.01); *G06F 19/3481* (2013.01); *G16H 10/60* (2018.01)

(58) Field of Classification Search
CPC .. G06F 19/345; G06F 19/322; G06F 19/3431; G06F 17/30702; G06Q 50/22; G06Q 50/24
See application file for complete search history.

(56) References Cited

U.S. PATENT DOCUMENTS

| | | |
|---|---|---|
| 7,809,660 B2 | 10/2010 | Friedlander et al. |
| 8,265,948 B2 | 9/2012 | Schmitt et al. |

(Continued)

FOREIGN PATENT DOCUMENTS

WO   WO-2014133825 A1 *   9/2014   ........... G06F 17/271

OTHER PUBLICATIONS

Milian et al., "Building a Library of Eligibility Criteria to Support Design of Clinical Trials." Knowledge Engineering and Knowledge Management,18th International Conference, EKAW; 2012; Publisher: Springer-Verlag; Country of Publication: Germany; ISSN: 9783642338755; Database: INSPEC; pp. 327-336.

(Continued)

*Primary Examiner* — Jonathan Durant
(74) *Attorney, Agent, or Firm* — Patterson + Sheridan, LLP

(57) ABSTRACT

System, method, and computer program product for evaluating attribute values to determine treatment eligibility, the method by receiving a set of required attributes associated with a treatment protocol, receiving a case, wherein the case includes a patient history containing patient attribute values, identifying a patient attribute value that does not satisfy a required attribute specified by the treatment protocol, determining a likelihood that the patient could meet the required attribute based upon the patient history, and providing an indication of the likelihood that the patient could satisfy the required attribute specified by the treatment protocol.

20 Claims, 5 Drawing Sheets

(56) References Cited

U.S. PATENT DOCUMENTS

| | | | |
|---|---|---|---|
| 8,533,008 B2 | 9/2013 | Kahn et al. | |
| 2006/0025931 A1* | 2/2006 | Rosen | G06F 19/00 |
| | | | 702/19 |
| 2007/0067189 A1* | 3/2007 | Boris | G06F 19/363 |
| | | | 705/3 |
| 2009/0164240 A1* | 6/2009 | Friedmann | G06F 19/363 |
| | | | 705/2 |
| 2012/0290328 A1 | 11/2012 | McCallie, Jr. et al. | |
| 2012/0316898 A1* | 12/2012 | Levitt | G06Q 50/24 |
| | | | 705/3 |
| 2013/0029307 A1* | 1/2013 | Ni | G06N 99/005 |
| | | | 434/322 |
| 2013/0132308 A1* | 5/2013 | Boss | G06F 17/30976 |
| | | | 706/12 |
| 2013/0288219 A1* | 10/2013 | Dheap | G09B 7/12 |
| | | | 434/350 |
| 2013/0332191 A1 | 12/2013 | Hoffman et al. | |
| 2014/0074510 A1* | 3/2014 | McClung | G06F 19/3431 |
| | | | 705/3 |
| 2014/0122113 A1* | 5/2014 | Hoffman, Jr. | G06Q 50/24 |
| | | | 705/2 |
| 2014/0316768 A1* | 10/2014 | Khandekar | G06F 17/30654 |
| | | | 704/9 |
| 2014/0316793 A1* | 10/2014 | Pruit | G06F 19/363 |
| | | | 705/2 |
| 2015/0058033 A1* | 2/2015 | Munos | G06F 19/363 |
| | | | 705/2 |

OTHER PUBLICATIONS

International Business Machines Corporation, "List of IBM Patents or Patent Applications Treated as Related," Jul. 21, 2015, 2 pages.

* cited by examiner

SYSTEM AND METHOD FOR WEIGHTING MANAGEABLE PATIENT ATTRIBUTES DURING CRITERIA EVALUATIONS FOR TREATMENT

CROSS-REFERENCE TO RELATED APPLICATION

This application is a continuation of co-pending U.S. patent application Ser. No. 14/630,751, filed Feb. 25, 2015. The aforementioned related patent application is herein incorporated by reference in its entirety.

BACKGROUND

Embodiments disclosed herein relate to computer software. More specifically, embodiments disclosed herein relate techniques for identifying criteria for a patient treatment, whether a patient meets the criteria, and whether the patient is likely to be able meet the required criteria if they do not currently meet the requirements.

Determining an appropriate treatment based on the patient is an important part of providing medical care. In order to have safe, relevant, and effective treatment, patients generally need to satisfy criteria before receiving a particular treatment. Criteria for each treatment typically varies and may include multiple attributes used to evaluate the suitability of a treatment for a given patient. Each attribute may specify an associated value or range which a patient should meet in order to qualify for a given treatment. Additionally, patient medical data may change over time or a course of treatment. Because of these factors, matching patients to treatments can be a time-consuming process. Accordingly, techniques for weighing manageable patient attributes during criteria evaluations for treatment are needed.

SUMMARY

Embodiments disclosed herein provide a system, method, and computer program product for evaluating attribute values to determine treatment eligibility, the method by receiving a set of required attributes associated with a treatment protocol, receiving a case, wherein the case includes a patient history containing patient attribute values, identifying a patient attribute value that does not satisfy a required attribute specified by the treatment protocol, determining a likelihood that the patient could meet the required attribute based upon the patient history, and providing an indication of the likelihood that the patient could satisfy the required attribute specified by the treatment protocol.

BRIEF DESCRIPTION OF THE SEVERAL VIEWS OF THE DRAWINGS

So that the manner in which the above recited aspects are attained and can be understood in detail, a more particular description of embodiments of the disclosure, briefly summarized above, may be had by reference to the appended drawings.

It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
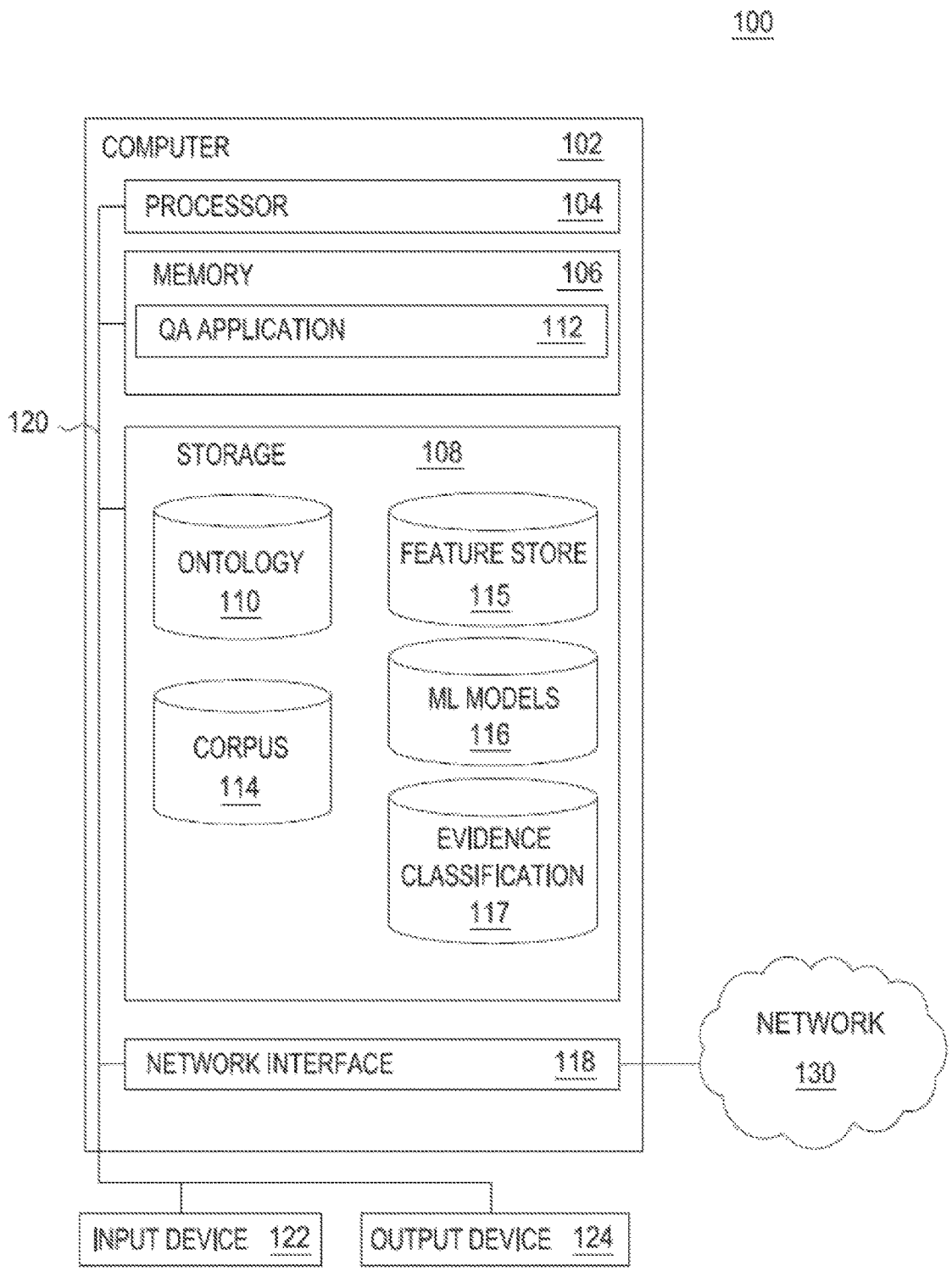
FIG. 1 is a block diagram illustrating a networked system for use in weighing manageable patient attributes during criteria evaluations for treatment according to one embodiment.

Embodiments disclosed provide techniques for identifying required criteria for a patient treatment protocols, determining whether a patient meets the required criteria, and predicting whether the patient is likely to be able meet the required criteria if they do not currently meet the required criteria. Patient treatments may include existing treatment options as well as clinical trials of new medications or techniques. Matching patients to clinical trials allows for safer and more effective clinical trials. Generally, the required criteria for a particular clinical trial treatment protocol includes attributes with an associated required value or range which must be met by the patient in order to participate. For example, a particular clinical trial may include a treatment protocol calling for patients under 50 years of age, where age is an attribute requiring a value under 50 for eligibility to participate in the trial. In such a case, a 51 year old person would not be able to participate in the trial. However, a second trial may require patients with a systolic blood pressure between 140 and 159. A patient with a blood pressure of 170, but starting blood pressure medication may be excluded from this second trial where an attribute range for blood pressure is strictly evaluated. To broaden the pool of eligible patients, when determining eligibility for a clinical trial, it may be desirable to include patients who do not strictly meet every required attribute of the treatment protocol, but may be able to meet the required attributes in the future. To determine which patients may be able to meet the required attributes, a patient's attributes may be evaluated and scored based upon how closely they align with the required attributes.

However, just because an attribute can be changed does not mean that the attribute can be changed for a particular patient. That is, it can be difficult to determine the likelihood that the particular patient's attribute value can be changed to meet a required attribute value. For example, a particular patient may have been unresponsive to multiple blood pressure medications and thus less likely to be able to adjust their blood pressure to the required range. Another patient may be steadily losing weight through a diet and exercise regime. Analyzing the medical history of the particular patient may therefore yield a more accurate estimate of whether a patient's attribute value may meet the required attribute value in the future.

Generally, embodiments disclosed herein provide techniques for identifying required criteria for a patient treatment, determining whether a patient currently meets the required criteria, and predicting whether the patient is likely to be able meet the required criteria if they do not currently meet the required criteria. An automated threshold value prediction system may process cases through an analysis "pipeline." A pipeline may represent the execution of various analysis programs, or engines, using both the medical history of a patient as well as the criteria for a treatment protocol of a clinical trial. Information about the criteria, including the required attributes associated with the treatment protocol, for a trial may be presented as either structured or unstructured data. With structured data, data conversion may be applied to the required attributes and attribute values. Unstructured data may also be processed using direct information analysis, for example, using natural language processing (NLP), of the data to extract the required attributes and required attribute values of the clinical trial. A pipeline may be created for each domain or problem space (e.g. a different pipeline is used for supporting cancer treatments, diagnoses, predicting opinions, etc.). Further, analysis engines themselves may be directed to a particular domain (e.g., identification of a tumor stage or size, identification of health issues, predicting opinions, etc.). Question and answer analysis within a pipeline may also include complex NLP algorithms, used, for example, to identify deep semantic relationships within the text.

The pipeline may also analyze the attributes of a patient and determine which attributes may change. While certain patient attributes are not variable and cannot change, other patient attributes can change over time. For example, the fact that a patient once broke their arm cannot change, but that patient's weight or blood pressure can change over time. That is, a patient's weight is manageable as the patient can control their weight such as through diet and exercise. Other patient attributes may be mutable as they may be changed through medical interventions. For example, a patient's blood pressure may be mutable through medication. Further, certain attributes may change over time, but this change may or may not matter depending on the required attribute value. For example a patient's age changes over time. For a trial where eligibility depends on whether a patient is currently under the given age, that the patient continues to age does not matter. However, where a trial requires participants within a certain age range, a patient may become eligible for the trial at a later date. The pipeline may take into account the information related to required attributes values in a given trial in order to determine which attributes that may change are relevant for the given trial.

A patient's eligibility for a particular clinical trial may be scored based on how close a match the patient's attribute values are to the particular trial's required attribute values as specified by the treatment protocol. Where a patient's attribute values all meet the required attribute values, the patient is deemed eligible for the trial. Where a patient's attribute values does not meet all the required attribute values specified by the treatment protocol, the deep QA system can make a determination of how likely a patient will be able to meet an attribute and score the patient based on the determination. The scoring phase of a deep QA system, such as IBM's Watson, may call various scoring algorithms to help identify an answer (or response) to a case. A scoring algorithm may generate one or more feature scores to indicate a measure of confidence for each answer. The deep QA system may also use a training phase to learn which features, or combinations of features, are best at predicting a correct answer for different questions. Once the deep QA system has been trained, questions flowing through the pipeline may use the machine-learned model for finding the most likely correct answer.

FIG. 1 is a block diagram illustrating a networked system 100 for use in weighing manageable patient attributes during criteria evaluations for treatment according to one embodiment. The system 100 includes a computer 102. The computer 102 may also be connected to other computers via a network 130. In general, the network 130 may be a telecommunications network and/or a wide area network (WAN). In a particular embodiment, the network 130 is the Internet.

The computer 102 generally includes a processor 104 connected via a bus 120 to a memory 106, a network interface device 118, a storage 108, an input device 122, and an output device 124. The computer 102 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 104 is included to be representative of a single CPU, multiple CPUs, a single CPU having multiple processing cores, and the like. Similarly, the memory 106 may be a random access memory. While the memory 106 is shown as a single identity, it should be understood that the memory 106 may comprise a plurality of modules, and that the memory 106 may exist at multiple levels, from high speed registers and caches to lower speed but larger DRAM chips. The network interface device 118 may be any type of network communications device allowing the computer 102 to communicate with other computers via the network 130.

The storage 108 may be a persistent storage device. Although the storage 108 is shown as a single unit, the storage 108 may be a combination of fixed and/or removable storage devices, such as fixed disc drives, solid state drives, removable memory cards or optical storage. The memory 106 and the storage 108 may be part of one virtual address space spanning multiple primary and secondary storage devices.

As shown, the memory 106 contains the QA application 112, which is an application generally configured to operate a deep question answering (QA) system. One example of a deep question answering system is Watson, by the IBM Corporation of Armonk, N.Y. A user may submit a case (also referred to as a question) to the QA application 112, which provides an answer to the case. In one embodiment, for example, the QA system may predict whether a patient may be able to change their patient attribute values to meet the required attribute values of a given treatment. The QA application 112 may execute a pipeline to generate the prediction, which may be returned to the user.

As shown, storage 108 contains an ontology 110, corpus 114, feature store 115, ML models 116, and evidence classification 117. The ontology 110 provides a structural framework for organizing information. An ontology formally represents knowledge as a set of concepts within a domain, and the relationships between those concepts. The corpus 114 is a body of information used by the QA application 112 to generate answers to cases. Evidence classification 117 stores relationships between evidence from the corpus 114, the question context, and the predictive features. Although depicted as a database, ontology 110, corpus 114, feature store 115, ML models 116, and evidence classification 117 may take any form sufficient to store data, including text files, xml data files, and the like. In one embodiment, the ontology 110 is part of the corpus 114. Although depicted as residing on the same computer, any combination of the QA application 112, the ontology 110, corpus 114, feature store 115, ML models 116, and evidence classification 117 may reside on the same or different computers.

The input device 122 provides input to the computer 102. For example, a keyboard and/or a mouse may be used. The output device 124 may be any device for providing output to a user of the computer 102. For example, the output device 124 may be any conventional display screen. Although shown separately from the input device 122, the output device 124 and input device 122 may be combined. For example, a display screen with an integrated touch-screen may be used.

Figure 2:
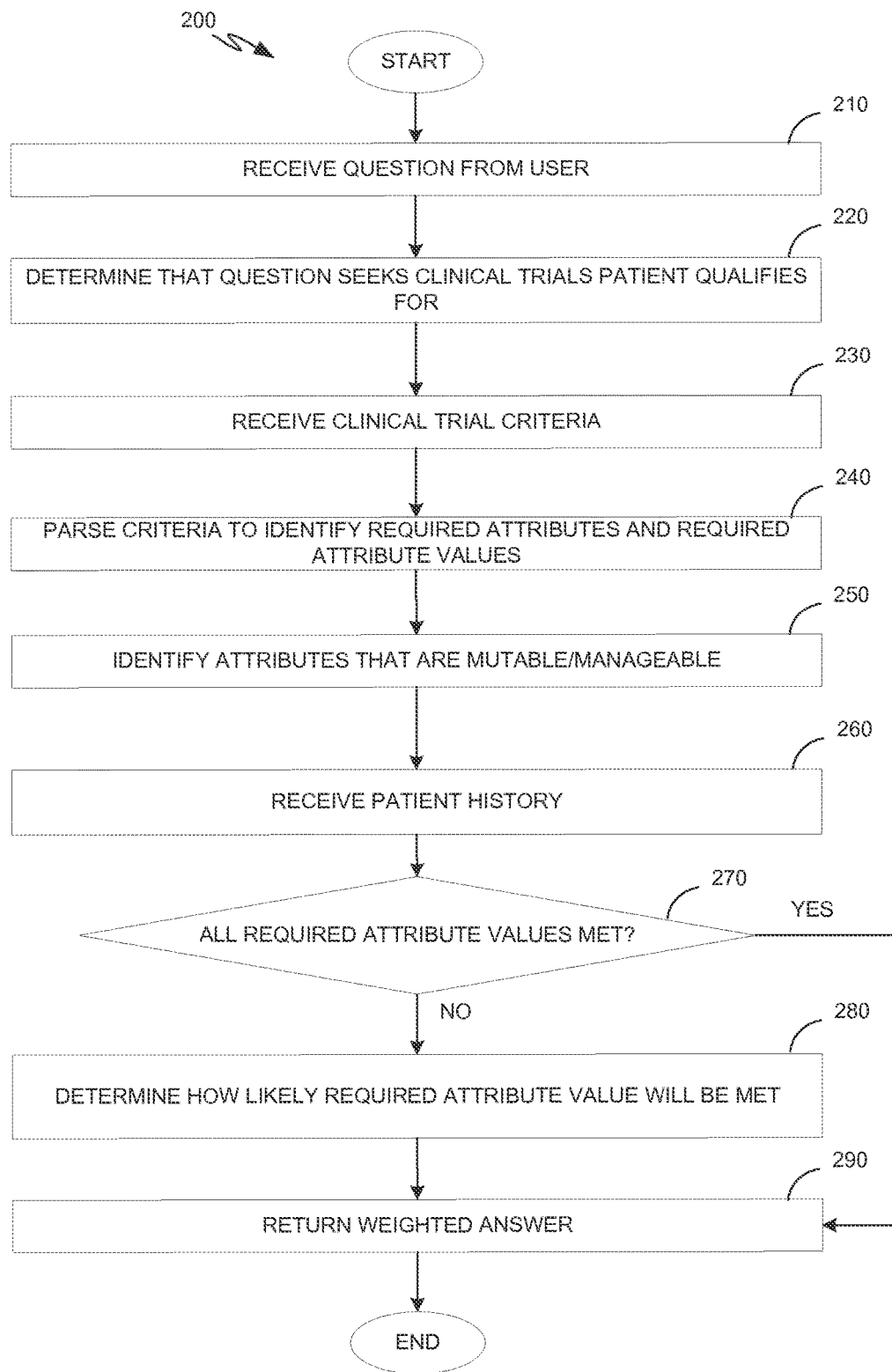
FIG. 2 is a flow chart illustrating a method for use in weighing manageable patient attributes during criteria evaluations for treatment according to one embodiment.

FIG. 2 is a flow chart illustrating a method 200 for use in weighing manageable patient attributes during criteria evaluations for treatment, according to one embodiment. At step 210, the QA application receives a question from a user seeking to determine the clinical trials a patient may be eligible for. At step 220, the QA application 112 determines that the question seeks to determine the clinical trials the patient is eligible to participate in. This may be done by processing the question to identify topics present in the question and identify what answer is being sought, e.g. whether a patient is eligible for a particular trial. A person may also be identified from the question. Any suitable method may be used to identify the question context, including the use of natural language processing (NLP) to extract normalized terms and concepts from the question. At step 230, the QA application 112 receives clinical trial criteria information. This information may be received from the user or previously stored in, for example, the corpus 114, and is associated with treatment protocols of a clinical trial, or a set of clinical trials. At step 240, the QA application 112 may parse the clinical trial criteria to identify attributes required by the trial along with the required attribute values. This information may be in the form of structured or unstructured data. Structured data is data formatted or marked up to make the information easier to parse by computers, such as with the addition of tagged or XML data fields. Where the clinical trial criteria is stored in structured data, the data may be converted into a data format compatible with the QA application 112. Unstructured data may be formatted for human readability and is not optimized for data input or modeling. Where the clinical trial criteria is specified using unstructured data, the QA application 112 may parse the data, using techniques such as NLP, to extract the required attributes and associated attribute values. At step 250, the QA application 112 may identify and label each required attribute that is mutable or manageable. This identification may be based upon, for example, database comparisons, predicative algorithms or earlier trained models of how mutable or manageable a given required attribute may be. At step 260, the QA application 112 receives a patient record. This patient record may also be structured or unstructured data. At step 270, the QA application determines whether the patient satisfies the required attribute values of a particular clinical trial. Step 270 is discussed in greater detail with reference to FIG. 3. If it is determined that the patient satisfies the criteria specified by the treatment protocol for a clinical trial, then the patient is marked as eligible to participate in the clinical trial. If there are additional clinical trial to evaluate for the patient, the method loops back to step 210. Otherwise, where the patient does not satisfy some of the required attribute values, the QA application, at step 280, determines how likely it is that each criteria not satisfied can (or will) be later met by the patient. Step 280 is discussed in greater detail with reference to FIG. 4. At step 290, the weighted answer is returned to the user indicating how likely the patient is to be eligible for the clinical trial. Where a patient meets all required attributes, the weighted answer may be the full weight (i.e. a maximum score) or simply an indication that the patient is qualified for the clinical trial. The weighted answer may also be processed for ease of use. For example, threshold may be set such that weights above a certain weight may result in an answer of "Potentially Eligible," "Probably Not Eligible," or the like.

Figure 3:
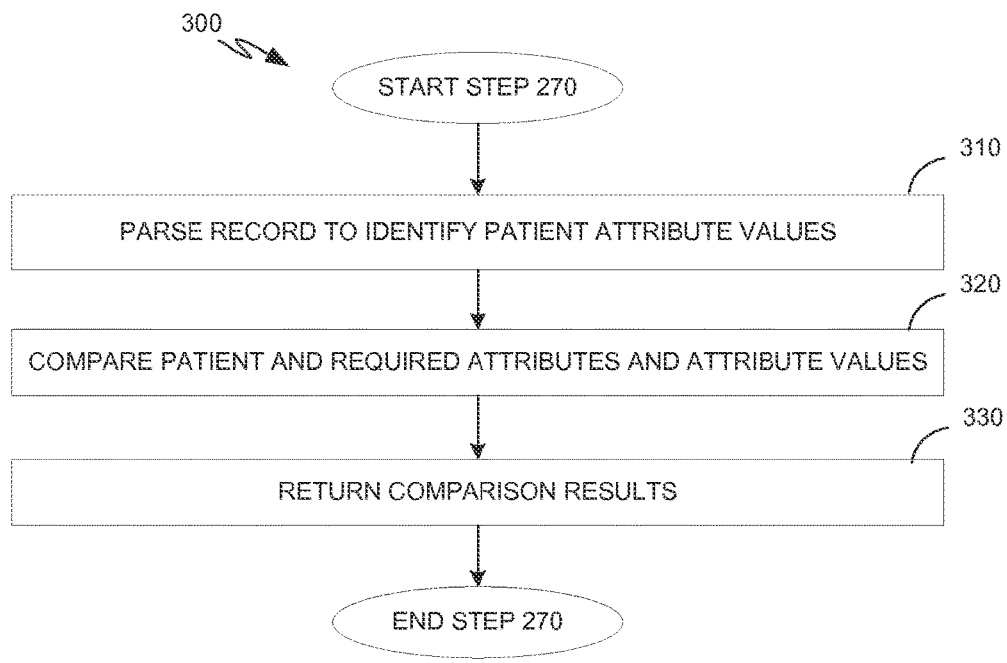
FIG. 3 is a flow chart illustrating a method for determining whether required attribute values are met according to one embodiment.

FIG. 3 is a flow chart illustrating a method 300 for determining whether required attribute values are met according to one embodiment. At step 310, the patient's medical record is parsed to extract values for the attributes used to determine eligibility of a patient to participate in a clinical trial. As with the clinical trial criteria, a patient's medical records may include both structured and unstructured data and may be parsed using techniques such as NLP, predicative algorithms and the like. In addition to the patient's current attribute values, previous values for some patient attributes may also be identified. At step 320, the attribute values identified in the patient's medical record are compared against the criteria for eligibility. The patient's eligibility for the clinical trial being evaluated is then scored based on the required attribute values met and the weights of those attributes. Scoring may comprise an aggregation score where scores are aggregated and when the patient's eligibility score reaches a particular threshold, the patient may be determined to be eligible for the trial. This threshold may be set such that all of the required attribute values are met to reach the threshold. The set of required attribute values that are not met by the patient may also be identified and stored. At step 330, the eligibility score along with attribute information are returned for further processing, if needed. The weighted answer may be based on the eligibility score.

Figure 4:
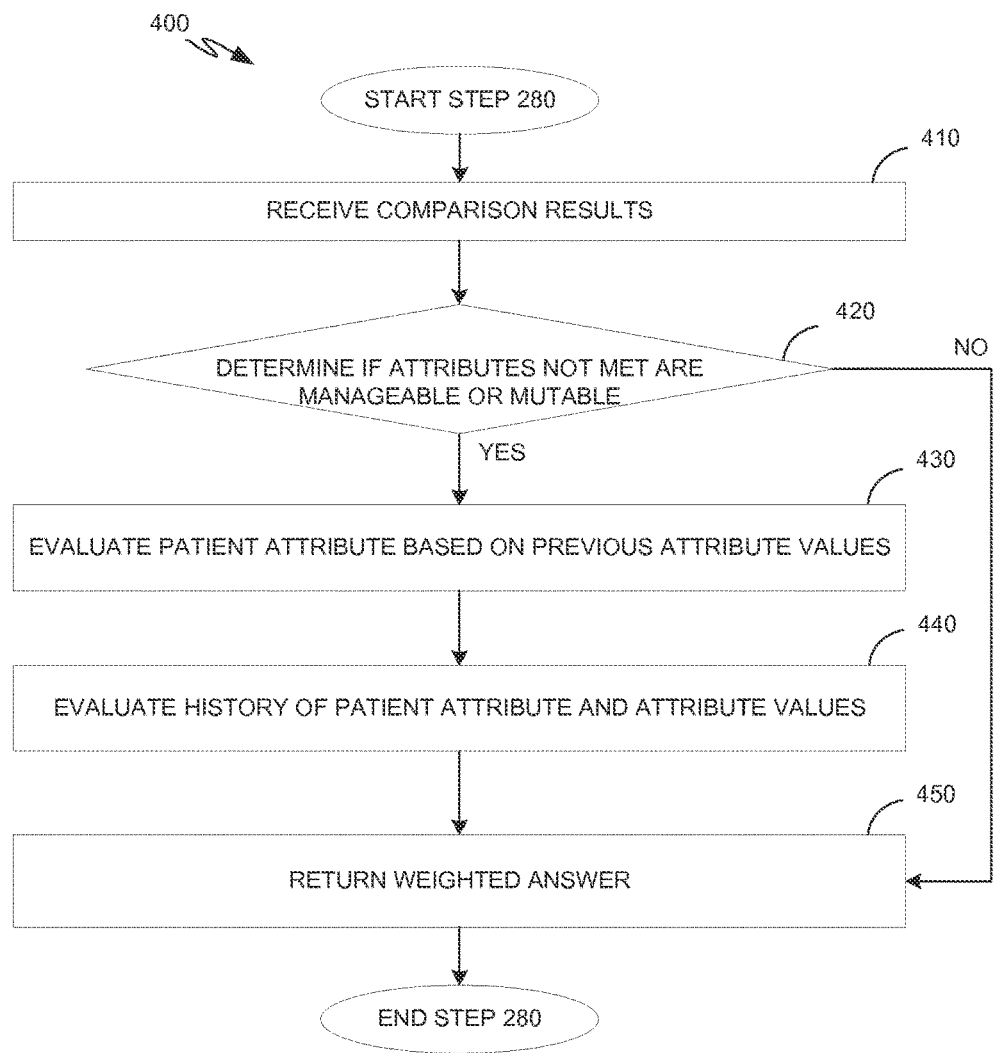
FIG. 4 is a flow chart illustrating a method for determining how likely a required attribute value will be met according to one embodiment.

FIG. 4 is a flow chart illustrating a method 400 for determining how a required attribute value will be met according to one embodiment. At step 410, the attribute values, criteria, and the parsed patient medical records are received. At step 420, attributes which the patient does not satisfy are evaluated based on whether they are mutable or manageable attributes with respect to the clinical trial. Where an attribute is determined to be unmanageable or immutable and the patient attribute does not satisfy the attribute, the QA application 112 returns an answer indicating that the patient is ineligible for the clinical trial.

At step 430, if any of the unmet required attributes are mutable or manageable attributes, the patient's past values for the attribute may be evaluated to determine how likely it is that the patient may satisfy the criteria for the mutable or manageable attribute in the future. The patient's eligibility score may be adjusted based on how far the patient's attribute value is from the required attribute value. For example, where the difference between the patient's attribute value and the required attribute value is large, the patient's eligibility score may be adjusted such that the patient is less likely to ever be eligible even if all other required attributes are met. Conversely, where the distance is smaller the patient's eligibility score may be adjusted such that the patient is more likely to eventually be eligible. Thus where a patient is 150 lbs under the required weight, all else being equal, the patient's eligibility score would be further from the eligibility threshold than if the patient were 2 lbs under the required weight. At step 440, the patient's attribute and attribute value history may be evaluated. The evaluation may include a time dimension and account for trends or changes to an attribute value over time. For example, where a patient is above a required weight, but the patient's weight is steadily trending down, the patient's eligibility score may be adjusted to reflect this progress. However, where a patient has an extensive medical history indicating the patient has never satisfied the required attribute value, the trend indicates that the patient is less likely to meet the required attribute values and the patient's eligibility score may be adjusted to reflect this. In comparison, where a patient's attribute value fluctuates over time between meeting and not meeting the required attribute value, the patient's eligibility score may be adjusted such that the patient is more likely to be eligible. Other factors may also be correlated to attribute values over time. Where a record reflects treatments or attempts to adjust an attribute, the eligibility score may be adjusted to take into account these factors. These factors may be associated with attribute values using, for example, data stored in the corpus, such as a medical treatment data. For example, a patient's medical record may indicate that the patient has taken several medications used for treating a particular attribute. Any recorded changes (if any) to the attribute value while the patient is on the medication may indicate how the patient responds to the medication and correlate to how manageable or mutable the attribute value may be for the patient. Treatments associated with managing or mutating the attribute value may also be compared against the required attribute values to avoid treatments with side-effects that may disqualify the patient for the trial.

Additionally, factors that influence the patient's eligibility score may be cumulative. That is, a first patient's fluctuating historical attribute value and a large difference between their attribute value and the required attribute value likely will be less likely to be eligible as compared to a second patient with a similarly fluctuating historical attribute value, but a small difference between their attribute value and the required attribute value. Other factors not directly related to a medical attribute may also be considered. For example, a patient's history may indicate how willing a patient is to travel to obtain treatment, or how willing to consent to various procedures may also be considered. At step 450, the patient's eligibility score may be returned as a weighted answer based on the eligibility score.

Figure 5:
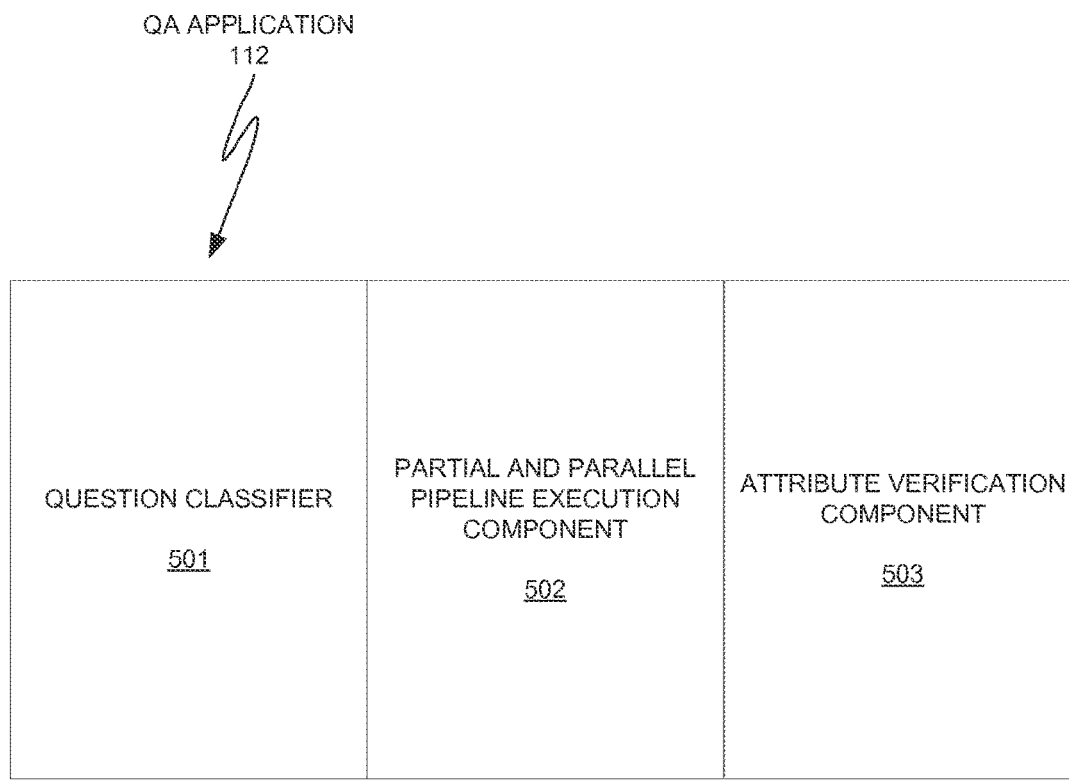
FIG. 5 is a block diagram illustrating components of a system for use in weighing manageable patient attributes during criteria evaluations for treatment according to one embodiment.

FIG. 5 is a block diagram illustrating components of a system for use in weighing manageable patient attributes during criteria evaluations for treatment according to one embodiment. In one embodiment, the deep question answering system is the QA application 112. As shown, the QA application 112 contains a question classifier component 501, a partial and parallel pipeline execution component 502, and an attribute verification component 503. The question classifier component 501 may parse questions to determine that the question seeks to identify trials in which a patient may be eligible for. Once identified, the topic may be stored in a feature store, such as feature store 115. The partial and parallel pipeline execution component 502 may, when presented with a case, access the topic defined in the feature store 115 to reduce processing of sources that do not discuss the topic identified. The attribute verification component 503 may identify relevant pieces of information from the patient medical records, parse the information, and store these pieces of information in the corpus 114.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the preceding, reference is made to embodiments of the disclosure. However, it should be understood that the disclosure is not limited to specific described embodiments. Instead, any combination of the preceding features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be used. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Embodiments of the disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access a deep question answering system or related data available in the cloud. For example, the deep question answering system could execute on a computing system in the cloud and provide question classification and feature mapping. In such a case, the deep question answering system could classify questions, map features and store the resultant data sets at a storage location in the cloud. Doing so allows a user to access this information from any computing system attached to a network connected to the cloud (e.g., the Internet).

While the foregoing is directed to embodiments of the present disclosure, other and further embodiments of the disclosure may be devised without departing from the basic scope thereof, and the scope thereof is determined by the claims that follow.

What is claimed is:

1. A computer-implemented method for evaluating attribute values to determine eligibility for a first treatment, the computer-implemented method comprising:

responsive to receiving input regarding a first patient, determining a topic based on parsing the received input using natural language processing, the topic comprising a request to identify treatment protocols for which the first patient can be eligible, wherein the topic is determined by a question classifier component of an application and stored in a feature store;

determining, based on a corpus and by a pipeline execution component of the application, a set of required attributes associated with a treatment protocol associated with the first treatment, wherein the pipeline execution component reduces processing of sources in the corpus that do not pertain to the stored topic;

responsive to receiving a case, wherein the case includes a patient history containing patient attribute values for the first patient, identifying, by an attribute verification component of the application, a first patient attribute value that does not satisfy a first attribute specified by the treatment protocol as a required attribute;

determining that the first patient is not currently eligible to receive the first treatment, based on determining that the first patient attribute value does not satisfy the first attribute specified by the treatment protocol;

upon determining that the first patient is not currently eligible to receive the first treatment, determining, by operation of one or more computer processors and based on evaluating the patient history using one or more machine learning models, a likelihood that the patient will meet the first attribute in the future due to a change in the first patient attribute value, thereby determining potential eligibility of the first patient for the treatment protocol with a greater measure of accuracy than absent determining the likelihood, wherein the likelihood is determined based on an upward or downward trend of the first patient attribute value and based further on an extent by which the first patient attribute value differs from the required attribute; and causing approval, based on the determined likelihood, of the first patient for receiving the treatment protocol, whereafter the treatment protocol is applied to the first patient, wherein absent determining the likelihood, the first patient would have been denied from receiving the treatment protocol.

2. The computer-implemented method of claim 1, further comprising evaluating the patient history using natural language processing to process the case and identify attribute values of the patient.

3. The computer-implemented method of claim 1, wherein determining the likelihood comprises determining whether the first attribute is mutable or manageable and returning an indication that the patient is ineligible to receive the first treatment if the first attribute is either immutable or unmanageable.

4. The computer-implemented method of claim 1, wherein determining the likelihood that the patient could satisfy the first attribute value is further based on comparing at least one attribute that is specified as required by the treatment protocol, and patient attribute values from the patient history.

5. The computer-implemented method of claim 1, wherein determining the likelihood is further based on determining whether the first patient attribute value in the patient history has ever satisfied the first attribute at a moment in time in the past.

6. The computer-implemented method of claim 1, wherein determining the likelihood is further based on determining whether the patient history indicates that the patient has previously undergone treatment that could change the value of the first patient attribute value, and any change in the first patient attribute value in response to the treatment.

7. The computer-implemented method of claim 6, wherein determining the likelihood is further based on determining whether the treatment is associated with a side-effect that may impact a second patient attribute value that corresponds to a second attribute specified by the treatment protocol as a required attribute, wherein the second patient attribute value currently satisfies the second attribute and the side-effect may cause the second patient attribute value to no longer satisfy the second attribute.

8. The computer-implemented method of claim 1, wherein the application is associated with an ontology and the one or more machine learning models, and wherein determining the likelihood that the patient could meet the first attribute in the future comprises processing the patient history using the one or more machine learning models.

9. The computer-implemented method of claim 8, wherein the at least a first of the one or more machine learning models is trained to generate a measure of confidence in the determined likelihood.

10. The computer-implemented method of claim 1, wherein determining the likelihood comprises determining whether the first attribute is mutable or manageable and returning an indication that the patient is ineligible to receive the first treatment if the first attribute is either immutable or unmanageable, wherein determining whether the first attribute is mutable or manageable comprises processing at least a first feature of the first attribute using the one or more machine learning models.

11. The computer-implemented method of claim 1, wherein the attribute verification component identifies, from medical records of the first patient, medical information relevant to determining the potential eligibility of the first patient for the treatment protocol;

wherein the application is associated with a plurality of data structures including the corpus, the feature store, an evidence classification, and the one or more machine learning models, wherein the corpus includes an ontology component, wherein the evidence classification specifies relationships between the corpus and the feature store;

wherein determining the likelihood that the patient could meet the first attribute in the future comprises processing the patient history using the one or more machine learning models, wherein the at least a first of the one or more machine learning models is trained to generate a measure of confidence in the determined likelihood.

12. The computer-implemented method of claim 11, wherein the likelihood is determined using a trained machine learning model of how mutable the first attribute is for a given patient over time, wherein an indication that the patient is ineligible to receive the first treatment is returned upon determining that the first attribute is immutable;

wherein determining the likelihood is further based on determining whether the first patient attribute value in the patient history has ever satisfied the first attribute at a moment in time in the past.

13. The computer-implemented method of claim 12, wherein determining the likelihood is further based on determining whether the patient history indicates that the patient has previously undergone treatment that could change the value of the first patient attribute value, and any change in the first patient attribute value in response to the treatment;

wherein determining the likelihood is further based on determining whether the treatment is associated with a side-effect that may impact a second patient attribute value that corresponds to a second attribute specified by the treatment protocol as a required attribute, wherein the second patient attribute value currently satisfies the second attribute and the side-effect may cause the second patient attribute value to no longer satisfy the second attribute.

14. The computer-implemented method of claim 13, wherein the computer-implemented method further comprises training the one or more machine learning models in order to ascertain which features of attributes are more accurate in predicting a correct answer for different questions, relative to other features of the attributes, whereafter the one or more machine learning models are used with one or more scoring algorithms in order to generate one or more feature scores to indicate a measure of confidence for each candidate answer to the specified question, wherein the potential eligibility of the first patient for the treatment protocol is determined based on the measure of confidence for each candidate answer to the specified question.

15. The computer-implemented method of claim 14, wherein the treatment protocol specifies a plurality of required attributes including the required attribute, the plurality of required attributes including patient age, patient blood pressure level, patient body weight, patient willingness to travel to obtain treatment, patient willingness to consent to medical procedures, and a count of treatment types previously tried by a given patient for a given medical condition, respectively.

16. The computer-implemented method of claim 1, wherein the required attribute is selected from patient age, patient blood pressure level, patient body weight, patient willingness to travel to obtain treatment, patient willingness to consent to medical procedures, and a count of treatment types previously tried by a given patient for a given medical condition.

17. The computer-implemented method of claim 1, wherein the treatment protocol specifies a plurality of required attributes including the required attribute, the plurality of required attributes including at least two attributes selected from patient age, patient blood pressure level, patient body weight, patient willingness to travel to obtain treatment, patient willingness to consent to medical procedures, and a count of treatment types previously tried by a given patient for a given medical condition.

18. The computer-implemented method of claim 1, wherein the treatment protocol specifies a plurality of required attributes including the required attribute, the plurality of required attributes including at least three attributes selected from patient age, patient blood pressure level, patient body weight, patient willingness to travel to obtain treatment, patient willingness to consent to medical procedures, and a count of treatment types previously tried by a given patient for a given medical condition.

19. The computer-implemented method of claim 1, wherein the treatment protocol specifies a plurality of required attributes including the required attribute, the plurality of required attributes including at least four attributes selected from patient age, patient blood pressure level, patient body weight, patient willingness to travel to obtain treatment, patient willingness to consent to medical procedures, and a count of treatment types previously tried by a given patient for a given medical condition.

20. The computer-implemented method of claim 1, wherein the treatment protocol specifies a plurality of required attributes including the required attribute, the plurality of required attributes including at least five attributes selected from patient age, patient blood pressure level, patient body weight, patient willingness to travel to obtain treatment, patient willingness to consent to medical procedures, and a count of treatment types previously tried by a given patient for a given medical condition.

* * * * *